United States Patent
Russo et al.

(10) Patent No.: US 8,889,654 B2
(45) Date of Patent: Nov. 18, 2014

(54) FOOD FORMULATION COMPRISING GLYCOGEN

(75) Inventors: Vincenzo Russo, Rome (IT); Elisa Liberati, Rome (IT); Giuseppe Biondi, Castel Gandolfo (IT); Roberta Petrosemolo, legal representative, Castel Gandolfo (IT); Enrica Biondi, legal representative, Nerviano (IT); Iacopo Biondi, legal representative, Castellanza (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 50 days.

(21) Appl. No.: 13/388,832

(22) PCT Filed: Jul. 29, 2010
(Under 37 CFR 1.47)

(86) PCT No.: PCT/EP2010/061002
§ 371 (c)(1),
(2), (4) Date: Apr. 11, 2012

(87) PCT Pub. No.: WO2011/015509
PCT Pub. Date: Feb. 10, 2011

(65) Prior Publication Data
US 2012/0220547 A1  Aug. 30, 2012

(30) Foreign Application Priority Data
Aug. 3, 2009 (EP) .................................. 09425315

(51) Int. Cl.
| | | |
|---|---|---|
| A23L 1/056 | (2006.01) | |
| A23L 1/30 | (2006.01) | |
| A23L 1/302 | (2006.01) | |
| A61K 31/716 | (2006.01) | |
| A61P 3/02 | (2006.01) | |

(52) U.S. Cl.
CPC ............... *A23L 1/30* (2013.01); *A23V 2002/00* (2013.01)
USPC ................. 514/54; 426/2; 426/648; 426/656; 426/658; 426/72

(58) Field of Classification Search
CPC .. A23L 1/30; A23V 2002/00; A23V 2200/00; A23V 2250/51; A23V 2250/2042
USPC ............................................. 514/54; 426/648
See application file for complete search history.

(56) References Cited

U.S. PATENT DOCUMENTS

| | | | |
|---|---|---|---|
| 5,597,913 A * | 1/1997 | Nicoletti et al. ............ 536/123.1 |
| 2005/0159329 A1 | 7/2005 | Fuertes et al. | |
| 2010/0063000 A1 * | 3/2010 | Furuyashiki et al. ............ 514/54 |
| 2010/0099864 A1 | 4/2010 | Van Der Maarel et al. | |
| 2010/0255083 A1 * | 10/2010 | Russo et al. ................... 424/452 |

FOREIGN PATENT DOCUMENTS

| | | |
|---|---|---|
| EP | 0 153 013 | 8/1985 |
| EP | 0 487 187 | 5/1992 |
| EP | 0 514 528 | 11/1992 |
| EP | 0 654 048 | 5/1995 |
| EP | 1 369 432 | 12/2003 |
| EP | 1 548 033 | 6/2005 |
| EP | 1 943 908 | 7/2008 |
| JP | 62 178505 | 8/1987 |
| JP | 63 290809 | 11/1988 |
| JP | 2008 1677 | 1/2008 |
| WO | 99 47120 | 9/1999 |
| WO | 00 32064 | 6/2000 |
| WO | 2004 023891 | 3/2004 |
| WO | 2008 081834 | 7/2008 |
| WO | WO2008081834 | * 7/2008 |

OTHER PUBLICATIONS

Whelan WJ. Enzymic Explorations of the Structures of Starch and Glycogen. Biochem J 122:609-622, 1971.*
Snell, F. D. et al., "Colorimetric Methods of Analysis", New York, vol. 3, p. 204, (1954).
International Search Report Issued Jun. 10, 2010 in PCT/EP10/061002 filed Jul. 29, 2012.

* cited by examiner

*Primary Examiner* — Brandon Fetterolf
*Assistant Examiner* — Yih-Horng Shiao
(74) *Attorney, Agent, or Firm* — Oblon, Spivak, McClelland, Maier & Neustadt, L.L.P.

(57) ABSTRACT

The present invention relates to a food formulation for the controlled release of glucose comprising glycogen and at least one other edible component, as well the use of glycogen for its preparation.

11 Claims, No Drawings

FOOD FORMULATION COMPRISING GLYCOGEN

SCOPE OF THE INVENTION

The present invention relates to the use of glycogen in the preparation of a food formulation for the controlled release of glucose.

In particular, the invention relates to the use of glycogen having an average molecular weight of over 2,000,000 Daltons in the preparation of an artificial food formulation for the controlled release of glucose.

STATE OF THE ART

Artificial food formulations comprising a source of glucose are well known in the art.

These formulations may have various fields of application.

A first field of application relates to use as dietary supplements for professional or amateur athletes.

A second field of application relates to use for parenteral administration, when the individual requiring treatment cannot be fed through the normal gastro-intestinal tract.

A third field of application relates to use for enteric feeding, in the form of liquids administered through cannulae directly into the stomach or intestine.

A fourth field of application relates to use as agents capable of inducing a feeling of satiety (bulking agent) without providing a significant caloric intake.

The artificial food formulations known in the art are generally obtained by the hydrolysis of starch or its derivatives. Starch is the most widespread polysaccharide in the plant world and comprises polymer chains of glucose. Starch mainly comprises two polymers, amylose (approximately 20% by weight) and amylopectin (approximately 80% by weight). Amylose is a linear polymer in which the glucose units are bound together by $\alpha(1 \rightarrow 4)$ glycoside bonds. Amylopectin is a branched polymer which has base chains of a structure similar to amylose on which side chains are branched through $\alpha(1 \rightarrow 6)$ bonds every 24-30 glucose units.

Patent applications EP1548033 or US 2005/0159329 describe highly branched polysaccharides obtained by the enzyme hydrolysis of starch having a mean molecular weight of between 90,000 and 150,000 Daltons. Similar polysaccharides having a mean molecular weight of between 3,500 and 20,000 Daltons are also described in patent application EP1369432.

Patent application EP487187 describes a food formulation comprising maltodextrins with a low calorie content of between 160 and 240 Kcal per 100 g. Patent application EP 514 528 describes a soluble dietary product comprising maltodextrins and beta-glucanes and/or pentosanes.

Maltodextrins are a class of substances derived from the hydrolysis of starch comprising a few tens of glucose molecules bound together by $\alpha(1 \rightarrow 4)$ glycoside bonds. Depending upon the degree to which the starch is hydrolysed, performed by chemical/physical or enzyme means or by a combination of both, various types of maltodextrins are obtained, distinguished by the number of glucose molecules making them up, typically from 2 to 20 units. Dextrose Equivalent (DE), which can run from a minimum of 4-6 to a maximum of 36-39, is determined on the basis of their length. The higher the DE value, the greater the degree of hydrolysis and the shorter the chain length. The final result of their digestion by the body is always glucose, but the rate at which the process takes place and the consequent production of energy depend on the DE value.

Artificial food formulations comprising a source of glucose contain other essential nutrient elements, for example for restoring water/salt balance in those situations where large quantities of sweat are produced, for example following physical effort or vigorous sporting activity.

The ideal osmolarity of these formulations should have a value which is identical to or slightly less than that of plasma (280-300 mOsml/kg), that is the energy solution should be hypotonic with blood, given that osmolarity influences the rate of gastric emptying and in particular the intestinal absorption of water and dissolved molecules. With maltodextrins it is possible to produce isotonic formulations comprising other nutrient elements in addition to a source of glucose.

The artificial food formulations known in the art, comprising low molecular weight polysaccharides with $\alpha(1 \rightarrow 4)$ bonds, provide a rapid supply of glucose which is quickly absorbed and metabolised.

This has two main types of disadvantages.

The first disadvantage lies in the fact that these food formulations cannot be administered to diabetic individuals because they would result in a rapid rise in blood glucose level (glycaemia).

The second disadvantage lies in the fact that the energy effect is not long-lasting unless large quantities of substances are ingested, which would result in diarrhoeic phenomena due to water being reclaimed by the intestine as a result of the excessive osmolarity of these substances.

Compositions having higher molecular weights and bonds which are more difficult to hydrolyse have been investigated in an attempt to overcome these disadvantages.

Patent application WO00/32064 describes a composition comprising a mixture of carbohydrates such as starch or starch derivatives, and cross-linked polysaccharides, such as derivatives of cellulose, gums, pectin and alginates.

Patent application WO2004/023891 describes a food formulation comprising polysaccharides with $\alpha(1 \rightarrow 6)$ bonds, typically dextran, pullulan and alternan, having a molecular weight of between 300,000 and 1,000,000 Daltons.

Patent application EP153013 describes formulations based on dextrans, polysaccharides with $\alpha(1 \rightarrow 6)$ bonds having a molecular weight between 50,000 and 1,000,000 Daltons, with little or no enteric absorption, which are capable of acting as agents capable of inducing a feeling of satiety (bulking agents).

The artificial food formulations known in the art comprising polysaccharides with $\alpha(1 \rightarrow 6)$ bonds are therefore known to provide a gradual release of glucose, provided that the chain length is not too long, in which case absorption is reduced drastically.

Glycogen is a polysaccharide of mainly animal origin which predominantly comprises molecules of D-glucose linked through $\alpha$-1-4 glucoside bonds with branches formed by $\alpha$-1-6 glucoside bonds every five-ten glucose units. The number and degree of branching of the glycogen vary according to the animal species from which it is obtained. The molecular weight of natural glycogen is of the order of $10^6$-$10^7$ Daltons. In nature glycogen is always bound to a protein, glycogenin, an enzyme related to the process of cell glycogen synthesis.

The quality of a commercial glycogen derivative derives from the presence of greater or lesser quantities of protein residues (measured in terms of quantities of nitrogen expressed as ppm) and reducing sugars. Patent EP 654048 describes a high quality glycogen derivative with a low nitrogen and reducing sugars content and a molecular weight of approximately 2,500,000 Daltons.

The glycogen is used as an emollient (as described in JP-A-87-178 505) and a hydrating agent (as described in JP-A-88-290 809) in the cosmetics sector, as an additive in the food sector, and as a humectant and lubricant in ophthalmic solutions (as described in patent WO99/47120).

SUMMARY OF THE INVENTION

Surprisingly, the Applicant has found that glycogen, in particular the glycogen described in patent EP654048, is capable of providing a gradual release of glucose similar to that obtained from other polysaccharides of lower molecular weight, of the maltodextrin type, in an in vitro system which mimics the gastro-intestinal tract.

The present invention therefore relates to the use of glycogen in the preparation of an artificial food formulation for the controlled release of glucose.

The Applicant has found that, despite its high molecular weight, over 2,000,000 Daltons, the abovementioned glycogen undergoes enzyme degradation through the enzymes present in the gastro-intestinal tract and allows glucose to be released gradually over a period of 20-24 hours, in an in vitro system which mimics the gastro-intestinal tract.

In addition to this, the Applicant has also observed that because the glycogen has a high molecular weight, over 2,000,000 Daltons, for the same quantity of glucose ingested, the osmolarity in comparison with the administration of maltodextrins is very much less, and this avoids the problems of the reclaim of water with the diarrhoeic effects known in the art.

The Applicant has also realised that the gradual and constant release of glucose observed during the transit of glycogen through the gastro-intestinal tract can advantageously provide the possibility of using suitably-dosed glycogen as a food or drink for diabetic individuals.

In another aspect this invention also relates to an artificial food formulation for the controlled release of glucose comprising glycogen and at least one other edible component, preferably at least one nutritional element.

The Applicant has found that the artificial food formulation according to the invention has greater palatability than a formulation known in the art containing maltodextrins.

In particular the Applicant has observed that the artificial food formulation according to the invention tastes less sweet, which is pleasanter and well tolerated by the palate.

Advantageously, the artificial food formulation according to this invention comprises at least one nutrient element selected from the group comprising carbohydrates, proteins, amino acids and derivatives, lipids, phospholipids, vitamins and mineral salts.

In a further aspect the present invention also relates to an aqueous formulation for the enteric or parenteral administration of glucose comprising glycogen and at least one further pharmaceutically-acceptable excipient.

The Applicant has found that the low osmolarity of the glycogen solutions makes it possible to prepare isotonic aqueous formulations (300 mOsm/kg) having a high glucose content, higher than the glucose content of known solutions containing sugars or polysaccharides of low molecular weight.

The Applicant has also found that, unlike other polysaccharides with slow glucose release, the glycogen solutions described above have pH values close to physiological values even with high polysaccharide concentrations.

DETAILED DESCRIPTION OF THE INVENTION

In particular, this invention relates to the use of glycogen in the preparation of an artificial food formulation for the controlled release of glucose.

The glycogen used in the present invention is obtained from the natural glycogen which can be extracted from animals or fungi. Molluscs, in particular mussels (*Mytilus edulis* and *Mytilus gallus provincialis*), are a particularly useful source of glycogen because they are available in large quantities at low cost and contain a certain amount of glycogen (on average between 2.5% and 3.9% by weight). Other natural sources of glycogen include other bivalve molluscs such as clams, oysters, some species of gastropods or sea snails, such as slipper limpets (*Crepidula fornicate*), and the organs of vertebrate animals which are rich in glycogen such as the liver and muscles.

Advantageously the glycogen used in the present invention has a molecular weight of over 2,000,000 Daltons, preferably between 2,000,000 and 5,000,000 Daltons.

Preferably, the glycogen used in this invention has a percentage of α-1-6 glucoside bonds of between 5% and 15%, preferably between 8% and 12%, in relation to the total number of bonds.

The glycogen used in the present invention may be used as obtained from the extraction processes or may be treated in subsequent purification procedures.

As already mentioned previously, the quality of a commercial glycogen derivative derives from the presence of a greater or lesser quantity of protein residues (measured in terms of quantities of nitrogen expressed in ppm) and reducing sugars.

For the purposes of the present invention it is preferred to use a glycogen derivative having a low reducing sugars and nitrogen content. Examples of commercial products preferably used in the present invention are glycogen derivatives produced and distributed by Sigma-Aldrich.

Preferably the glycogen derivative used in the present invention comprises less than 1% by weight, more preferably less than 0.25% by weight of reducing sugars, measured using the method by F.D. Snell and Snell, "Colorimetric Methods of Analysis", New York, 1954, Vol. III, p. 204).

Preferably the glycogen derivative used in the present invention comprises less than 3,000 ppm of nitrogen, more preferably less than 1,000 and even more preferably less than 100 ppm of nitrogen, measured according to the Kjeldahl method.

Preferably, the glycogen derivative used in the present invention is Polglumyt™ Glycogen, the trade name of a deproteinated glycogen having a low reducing sugars content produced and distributed by A.C.R.A.F. S.p.A. Rome, Italy and obtained according to the purification procedure described in patent EP 654048B1.

Advantageously, the glycogen derivative used in the present invention has a molecular weight of more than 2,000,000 Daltons, preferably between 2,000,000 and 5,000,000 Daltons, and a percentage of α-1-6 glucoside bonds of between 5% and 15%, preferably between 8% and 12%, relative to the total number of bonds.

The food formulation for the controlled release of glucose according to the present invention comprises glycogen and at least one other edible component, preferably at least one nutrient element.

Advantageously, the food formulation according to the present invention comprises at least one nutrient element selected from the group comprising carbohydrates, proteins, amino acids and derivatives, lipids, phospholipids, vitamins and mineral salts.

Preferably, the intake of carbohydrates in the food formulation according to the present invention is satisfied by the presence of glycogen. Nevertheless the food formulation according to the present invention may optionally comprise other types of carbohydrates in addition to glycogen.

The proteins used in the food formulation according to the present invention may be obtained from different natural sources, such as for example milk proteins, egg proteins, or blood proteins. The proteins may also be present in a hydrolysed form of peptides or individual amino acids. Preferably at least half the protein content is represented by intact proteins.

The lipids used in the food formulation according to the present invention may be triglycerides of saturated and unsaturated fatty acids containing 12 to 18 carbon atoms. Preferably triglycerides of long chain polyunsaturated fatty acids are used, such as for example ω-3, ω-6 and ω-9 fatty acids. Triglycerides of oleic acid, linoleic acid (LA), α-linolenic acid (ALA), arachidonic acid, eicosapentaenoic acid (EPA), docosahexaenoic acid (DHA) and docosapentaenoic acid (DPA) are particularly preferred. The phospholipids may be preferably lecithin or its equivalents. The lecithin may be of animal or plant origin and predominantly comprises phosphoric acid, choline, fatty acids, glycerol, glycolipids, triglycerides and phospholipids such as phosphatidylcholine, phosphatidylethanolamine and phosphatidylinositol.

The vitamins used in the food formulation according to the present invention are not particularly restricted, and may be any of the known vitamins such as, for example, water-soluble vitamins in groups B (B1, B2, B3, B5, B6, B8, B9 and B12) and C, or liposoluble vitamins in groups A, D, E and K. Pseudovitamins such as choline, anthranilic acid, lipoic acid, bioflavonoids, ubiquinones, and methylmethionine may also be used. The vitamins content of a formulation is generally expressed as a percentage of the Recommended Daily Allowance or RDA %.

Mineral salts are generally classified on the basis of the daily requirement as macroelements (over 100 mg), microelements (1 and 100 mg) and oligoelements (less than 1 mg). Macroelements are salts comprising calcium, chlorine, phosphorus, magnesium, potassium, sodium and/or sulphur. Microelements are salts comprising copper, zinc, fluorine, iodine, selenium, chromium, cobalt, manganese, molybdenum, silicon, nickel, vanadium. Oligoelements are salts comprising tin, nickel, germanium, vanadium and tungsten.

The food formulation may be in the form of a complete foodstuff, a food supplement, a nutritional solution for gastroenteric administration, for example for enteric feeding administered through a naso-gastric and naso-enteric tube, a nutritional solution for parenteral administration, or a foodstuff or supplement for diabetic individuals.

A complete foodstuff comprises all the nutritional substances necessary to satisfy the user's daily requirements in terms of the intake of substances and energy. Thus the formulation must contain carbohydrates, including glycogen, in a quantity of between 30% and 70% by weight, proteins in a quantity between 10% and 30% by weight and lipids between 20% and 40% by weight.

In addition to this the formulation must be capable of providing between 2000 and 2900 kcal per day, and may be in the form of a solid, for dissolution or dispersion in water or other beverage, or a liquid, in a form which is ready for use or as a concentrate. Lesser or greater energy intake may be provided for particular situations (dietary or sporting regimens).

A food supplement contains only some of the nutritional substances required to satisfy the user's daily requirements in terms of proteins and energy intake. Thus the formulation will be capable of providing less than 1500 kcal, preferably from 100 to 1000 kcal per day. Again in this case the formulation may be in solid or liquid form as described above, for addition to normal diet or as a component of normal diet.

The food formulation according to the present invention may contain further conventional food additives to improve its appearance, pleasantness and preservation, such as for example colouring agents, preservatives, antioxidants, acidity regulators, thickeners, stabilisers, emulsifiers, flavour enhancers, flavourings, humectants and sweeteners.

In one embodiment of the invention, the food formulation as discussed above is characterized in that the controlled release of glucose is such that about 50% of glucose is released in not less than 1 hour, preferably not less than 3 hours, more preferably not less than 5 hours. In another embodiment of the invention, the controlled release of glucose is such that about 80% of glucose is released in not less than 6 hours, preferably not less than 9 hours, more preferably not less than 12 hours.

The following examples will serve to illustrate the invention without however restricting it.

EXAMPLE 1

A model simulating the digestive system consisting in a first stage of incubation with salivary alpha-amylase, a second phase of incubation with pepsin and a third stage of incubation with pancreatin, amyloglucosidase and bovine bile at a pH of approximately 7 was prepared in the laboratory.

6 g of substrate were dissolved, in 250 ml Pyrex bottles provided with screw caps, in 100 ml of phosphate buffer.

The temperature of the solution was raised to 37° C., and then 0.1 ml of a solution of human alpha-amylase (solution A) was added. The resulting solution was incubated for 15 minutes in a bath thermostated to 37° C., with magnetic stirring.

The solution was adjusted to pH=2 with 2.50 ml of a 1 M solution of HCl, and then 0.25 ml of a suspension of Sigma P7012 pepsin in NaCl solution (solution B) was added. The resulting solution was incubated for 30 minutes at 37° C., again with magnetic stirring.

The solution was adjusted to pH=6.9 with 8.67 ml of a 1 M solution of $NaHCO_3$, and then 2 ml of a solution of Pancreatin and Amyloglucosidase in 25 mM $CaCl_2$ (Solution C) and 2.4 g of Bovine-Ovine Bile (Sigma B8381) were added. The resulting solution was incubated for 5 minutes at 37° C., with stirring.

The solution was transferred to dialysis tubes (mixed cellulose esters, cut-off 3500) which were placed in 1000 ml containers of a USP XIII dissolution apparatus containing approximately 900 ml of a buffer solution at a temperature of 37° C., prepared as follows:

800 ml of phosphate buffer and 0.8 ml of a 1 mM solution of $CaCl_2*2H_2O$ were mixed together. This was then adjusted to pH 2 with 20 ml of 1 M HCl, 2 ml of a NaCl solution (9 g/L) were added, the pH was adjusted to 6.9 with 70 ml of a 1 M $NaHCO_3$ solution and 16 ml of a solution of 25 mM $CaCl_2*2H_2O$ solution were added.

Over a 24-hour period 1 ml samples were taken from the buffer solution at the times indicated in Tables 2-5.

The test was carried out in duplicate using Polglumyt™ Glycogen and Maltodextrin DE 16.5-19.5 as a substrate. The 6 g of Polglumyt™ Glycogen sample is equivalent to 5.220 g of glucose, while the 6 g sample of Maltodextrin DE 16.5-19.5 is equivalent to 5.748 g of glucose.

The phosphate buffer and solutions A, B and C have the compositions in Table 1 below.

TABLE 1

| | |
|---|---|
| Phosphate buffer | 20 mM, pH = 6.9, $Na_2HPO_4$ 1.42 g/L, $KH_2PO_4$ 1.36 g/L, NaCl 0.58 g/L |
| Solution A | Sigma A1031 human alpha-amylase, 10 mg/ml in 1 mM $CaCl_2*2H_2O$ |

TABLE 1-continued

| | |
|---|---|
| Solution B | Sigma P7012 pepsin from porcine gastric mucosa, 1 mg/ml in a 9 g/L NaCl solution |
| Solution C | Sigma P7545 pancreatin, 0.5 mg/ml, Sigma A9228 amyloglucosidase (from *Rhizopus* SP) 840 U/ml in a 25 mM $CaCl_2 \cdot 2H_2O$ solution |

The samples were analysed to determine the quantity of glucose released, using two commercial kits: Sigma GAGO20 Glucose (GO) Assay Kit and Sigma GAHK20 Glucose (HK) Assay Kit (both supplied by Sigma-Aldrich Co.).

The first test is based on the oxidation of D-glucose to D-gluconic acid and hydrogen peroxide by means of glucose-oxidase. The hydrogen peroxide released reacts with the o-dianisidine in the presence of a peroxidase to form a brown oxidation product which in the presence of sulphuric acid yields an oxidation product of a pink colour. The intensity of the colour measured at 540 nm is proportional to the glucose concentration.

The results obtained are summarised in Tables 2-5 below.

TABLE 2

Maltodextrin DE 16.5-19.5 - Test 1

| Hours | mg/ml Glucose | % Glucose released |
|---|---|---|
| 0 | 0.00 | 0 |
| 2 | 0.81 | 14 |
| 3 | 1.52 | 27 |
| 4 | 1.99 | 35 |
| 6 | 2.58 | 46 |
| 20 | 3.85 | 68 |
| 21 | 3.96 | 70 |
| 24 | 4.02 | 71 |

TABLE 3

Maltodextrin DE 16.5-19.5 - Test 2

| Hours | mg/ml Glucose | % Glucose released |
|---|---|---|
| 0 | 0.00 | 0 |
| 2 | 0.89 | 16 |
| 3 | 1.79 | 32 |
| 4 | 2.28 | 40 |
| 6 | 2.96 | 53 |
| 20 | 4.22 | 75 |
| 21 | 4.08 | 73 |
| 24 | 4.10 | 73 |

TABLE 4

Polglumyt ™ Glycogen - Test 1

| Hours | mg/ml Glucose | % Glucose released |
|---|---|---|
| 0 | 0.00 | 0 |
| 2 | 0.74 | 14 |
| 3 | 1.16 | 23 |
| 4 | 1.90 | 37 |
| 6 | 2.57 | 50 |
| 20 | 4.12 | 80 |
| 21 | 4.14 | 81 |
| 24 | 4.12 | 81 |

TABLE 5

Polglumyt ™ Glycogen - Test 2

| Hours | mg/ml Glucose | % Glucose released |
|---|---|---|
| 0 | 0.00 | 0 |
| 2 | 0.82 | 16 |
| 3 | 1.23 | 24 |
| 4 | 2.08 | 41 |
| 6 | 2.43 | 47 |
| 20 | 4.14 | 81 |
| 21 | 4.05 | 79 |
| 24 | 4.01 | 78 |

The second test is based on the phosphorylation of glucose in the presence of ATP by means of a hexokinase. Glucose-6-phosphate is subsequently oxidised to 6-phosphogluconate in the presence of NAD (nicotinamide adenine dinucleotide), a reaction catalysed by glucose-6-phosphate dehydrogenase. In the course of the oxidation an equimolar quantity of NAD is reduced to NADH. The consequent increase in absorbance at 340 nm is directly proportional to the glucose concentration.

The results obtained are summarised in Tables 6-9 below.

TABLE 6

Maltodextrin DE 16.5-19.5 - Test 1

| Hours | mg/ml Glucose | % Glucose released |
|---|---|---|
| 0 | 0.00 | 0 |
| 2 | 0.96 | 17 |
| 3 | 1.60 | 28 |
| 4 | 2.21 | 39 |
| 6 | 2.73 | 49 |
| 20 | 4.09 | 73 |

TABLE 7

Maltodextrin DE 16.5-19.5 - Test 2

| Hours | mg/ml Glucose | % Glucose released |
|---|---|---|
| 0 | 0.00 | 0 |
| 2 | 0.89 | 16 |
| 3 | 1.82 | 32 |
| 4 | 2.30 | 41 |
| 6 | 3.04 | 54 |
| 20 | 4.49 | 80 |

TABLE 8

Polglumyt ™ Glycogen - Test 1

| Hours | mg/ml Glucose | % Glucose released |
|---|---|---|
| 0 | 0.00 | 0 |
| 2 | 0.83 | 16 |
| 3 | 1.44 | 28 |
| 4 | 2.03 | 40 |
| 6 | 2.75 | 54 |
| 20 | 4.07 | 80 |
| 24 | 4.14 | 81 |

TABLE 9

| | Polglumyt ™ Glycogen - Test 2 | |
|---|---|---|
| Hours | mg/ml Glucose | % Glucose released |
| 0 | 0.00 | 0 |
| 2 | 0.83 | 16 |
| 3 | 1.44 | 28 |
| 4 | 2.03 | 40 |
| 6 | 2.75 | 54 |
| 20 | 4.07 | 80 |

EXAMPLE 2

Six solutions of Polglumyt™ Glycogen and Maltodextrin DE 16.5-19.5 were prepared in distilled water, in increasing concentrations (10, 14, 18, 22, 26 and 30% by weight).

The resulting solutions were analysed to determine viscosity, pH, conductivity and osmolarity. The results are summarised in Tables 10 and 11 below, together with dissolution time. Viscosity measurements were performed using a Bohlin Gemini 150 rheometer provided with a 2°/55 mm cone-plate geometry. The osmolarity measurements were performed using a Knauer osmometer. Before analysis the solutions were filtered using a 0.2 μm Millipore filter.

TABLE 10

| | Polglumyt ™ Glycogen | | | | |
|---|---|---|---|---|---|
| Concentration (% w/w) | Dissolution time (min) | Viscosity (mPa) | pH | Conductivity (μS/cm) | Osmolarity (mOsm/kg) |
| 10 | 15 | 2.3 | 6.76 | 92.4 | −2.00 |
| 14 | 20 | 2.7 | 7.15 | 98.7 | −2.66 |
| 18 | 30 | 3.8 | 7.34 | 113.7 | 1.00 |
| 22 | 45 | 4.0 | 7.47 | 129.7 | 0.50 |
| 26 | 60 | 6.0 | 8.22 | 142.3 | 5.66 |
| 30 | 60 | 19.1 | 8.34 | 151.2 | 6.33 |

TABLE 11

| | Maltodextrin DE 16.5-19.5 | | | | |
|---|---|---|---|---|---|
| Concentration (% w/w) | Dissolution time (min) | Viscosity (mPa) | pH | Conductivity (μS/cm) | Osmolarity (mOsm/kg) |
| 10 | 1 | 1.96 | 5.41 | 560 | 110.30 |
| 14 | 1 | 2.15 | 4.65 | 707 | 152.00 |
| 18 | 1 | 2.33 | 4.56 | 792 | 193.30 |
| 22 | 1.5 | 2.71 | 4.22 | 850 | 236.00 |
| 26 | 2 | 2.98 | 4.46 | 916 | 290.66 |
| 30 | 2 | 3.53 | 4.41 | 937 | 335.00 |

EXAMPLE 3

The following Tables 12, 13 and 14 illustrate examples of artificial food compositions comprising glycogen according to the present invention. Table 12 illustrates a food formulation for normal individuals, Table 13 for diabetic individuals and Table 14 for administration via gastro-enteric tube.

TABLE 12

| Ingredients | | F1 | F2 | F3 |
|---|---|---|---|---|
| Polglumyt ™ Glycogen | g | 15 | 30 | 15 |
| Dextrose | g | 5 | 10 | 5 |
| Proteins | g | 20 | 10 | |
| Bcaa | g | 3 | | 1.5 |
| Creatine ethyl ester | g | | | 3 |
| Arginine | g | | | 2 |
| Ornithine | g | | | 1 |
| Citrulline | g | | | 0.25 |
| Glutamine | g | 3 | 2 | |
| Tyrosine | g | | | 0.5 |
| Taurine | g | | 0.5 | 0.5 |
| Magnesium | mg | | 25 | |
| Sodium | mg | | 345 | |
| Potassium | mg | | 145 | |
| Chlorides | mg | | 130 | |
| Alfa-lipoic acid | mg | 200 | | |
| Caffeine | mg | | | 60 |
| Tribulus Terrestris Ex | mg | | | 300 |
| Glucosamine | mg | 200 | 200 | |
| Curcuma Longa Ex | mg | 100 | | |
| Vitamin B1 | % RDA | 50% | 50% | 50% |
| Vitamin B2 | % RDA | 50% | 50% | 50% |
| Vitamin B5 | % RDA | 50% | 50% | 50% |
| Vitamin B6 | % RDA | 50% | 50% | 50% |
| Vitamin B12 | % RDA | 50% | 50% | 50% |
| Vitamin A | % RDA | 50% | 50% | 50% |
| Vitamin C | % RDA | 200% | 200% | 100% |
| Vitamin E | % RDA | 200% | 200% | 100% |

RDA: Recommended Daily Allowance
Polglumyt ™: Deproteinated glycogen having a reduced content of reducing sugars produced and distributed by A.C.R.A.F. S.p.A., Rome, Italy.

TABLE 13

| Ingredients | | F4 |
|---|---|---|
| Polglumyt ™ glycogen | g | 12 |
| Fructose | g | 1 |
| Proteins | g | 4 |
| Plant lipids | g | 3.7 |
| Dietary fibre | g | 1.5 |
| Vitamins | g | 100% RDA |
| Mineral salts | mg | 600 |

TABLE 14

| Ingredients | | F5 |
|---|---|---|
| Polglumyt ™ glycogen | g | 15 |
| Dextrose | g | 5 |
| Proteins | g | 6 |
| Plant lipids | g | 6 |
| Dietary fibre | g | 2 |
| Vitamins | g | 100% RDA |
| Mineral salts | mg | 600 |

EXAMPLE 4

Table 15 below illustrates an example composition for parenteral administration comprising glycogen according to the present invention.

TABLE 15

| Active ingredients | Quantities per 100 ml |
|---|---|
| Polglumyt ™ glycogen | 6 g |
| Dextrose | 1 g |
| Purified soya oil | 3.5 g |
| Alanine | 0.33 g |

TABLE 15-continued

| Active ingredients | Quantities per 100 ml |
| --- | --- |
| Arginine | 0.23 g |
| Aspartic acid | 0.07 g |
| Glutamic acid | 0.11 g |
| Glycine | 0.16 g |
| Histidine | 0.14 g |
| Isoleucine | 0.11 g |
| Leucine | 0.16 g |
| Lysine | 0.18 g |
| Methionine | 0.11 g |
| Phenylalanine | 0.11 g |
| Proline | 0.14 g |
| Serine | 0.09 g |
| Threonine | 0.11 g |
| Tryptophan | 0.04 g |
| Tyrosine | 0.004 g |
| Valine | 0.15 g |
| Calcium chloride | 0.01 g |
| Magnesium sulphate | 0.03 g |
| Potassium chloride | 0.12 g |
| Sodium acetate | 0.1 g |

EXAMPLE 5

Table 16 below illustrates an example composition in powder for dissolution in 100 ml of water for injectable preparations comprising glycogen according to the present invention.

TABLE 16

| Active ingredients | Quantities per 100 ml |
| --- | --- |
| Polglumyt ™ glycogen | 6 g |
| Dextrose | 1 g |
| Alanine | 0.77 g |
| Arginine | 0.61 g |
| Glycine | 0.92 g |
| Histidine | 0.25 g |
| Isoleucine | 0.92 g |
| Leucine | 1.13 g |
| Lysine | 0.62 g |
| Methionine | 0.10 g |
| Phenylalanine | 0.10 g |
| Proline | 0.82 g |
| Serine | 0.51 g |
| Threonine | 0.46 g |
| Tryptophan | 0.08 g |
| Valine | 0.86 g |

EXAMPLE 6

Table 17 below shows osmolarity values for 5% solutions of glucose, maltodextrin (DE 16.5-19.5) and Polglumyt™ glycogen.

TABLE 17

| Carbohydrate | Quantity g/100 ml | Osmolarity mOsm/kg | Units in mOsm/kg available for other components |
| --- | --- | --- | --- |
| Glucose | 5 | 280 | ~20 |
| Maltodextrin | 5 | 55 | ~245 |
| Polglumyt ™ glycogen | 5 | <1 | ~300 |

The results illustrated in Table 17 clearly show that a formulation containing approximately 5% of D-glucose is already an iso-osmotic solution, a 5% solution of maltodextrin (DE 16.5-19.5) has an osmolarity of 55 mOsm/kg (approximately ⅕ in comparison with glucose), while a 5% solution of Polglumyt™ glycogen has an osmolality value of less than 1 mOsm/kg (approximately 300 times less than glucose).

Thus, as illustrated in Table 17, a formulation containing Polglumyt™ Glycogen allows to prepare formulations having a higher glucose content and/or a higher content of essential nutrient components (for example vitamins, amino acids, mineral salts, etc.).

The invention claimed is:
1. An artificial food formulation, comprising:
   30 to 70% by weight of carbohydrate;
   10 to 30% by weight of protein;
   20 to 40% by weight of lipid;
   a glycogen; and
   an additional edible component not comprising glycogen,
   wherein the glycogen has a molecular weight of more than 2,000,000 Daltons and up to 5,000,000 Daltons, and a percentage of α-1-6 glucoside bonds between 5% and 15%, relative to a total number of glucoside bonds, wherein the glycogen comprises less than 1 %by weight of reducing sugars and less than 3,000 ppm of nitrogen, and wherein, when consumed, the food formulation has a controlled release of glucose units from the glycogen such that (1) about 50% of the glucose units are released from the glycogen in not less than 5 hours and/or (2) about 80% of the glucose units are released from the glycogen in not less than 12 hours.
2. The food formulation of claim 1, wherein the glycogen has a molecular weight from above 2,000,000 up to 2,500,000 Daltons.
3. The food formulation of claim 1, wherein the glycogen has a percentage of α-1-6 glucoside bonds between 8% to 12% relative to a total number of glucoside bonds.
4. The food formulation of claim 1 being in solid form or in an aqueous solution.
5. The food formulation of claim 1, which is a complete foodstuff, a food supplement, a nutritional solution for gastroenteric administration, a nutritional solution for parenteral administration, a foodstuff for a diabetic individual, or a supplement for a diabetic individual.
6. A method for producing the artificial food formulation according to claim 1, the method comprising: mixing a glycogen and an edible component not comprising glycogen.
7. The method of claim 6, wherein the glycogen has a molecular weight of more than 2,000,000 Daltons and up to 5,000,000 Daltons, and a percentage of α-1-6 glucoside bonds between 5and 15% relative to a total number of glucoside bonds.
8. The method of claim 7, wherein the food formulation is in solid form or in an aqueous solution.
9. The method of claim 7, wherein the food formulation is at least one selected from the group consisting of a complete foodstuff, a food supplement, a nutritional solution for gastroenteric administration, a nutritional solution for parenteral administration, a foodstuff for a diabetic individual, and a supplement for a diabetic individual.
10. The food formulation of claim 1, wherein the glycogen comprises less than 0.25% by weight of reducing sugars and less than 1,000 ppm of nitrogen.
11. A method for controlling a release of glucose units from a glycogen, the method comprising: administering to a patient in need thereof an effective amount of the food formulation of claim 1, wherein a release of glucose units from the glycogen in the food formulation, after the administering, is about 50% in not less than 5 hours.

* * * * *